(12) United States Patent
Wilson, Jr.

(10) Patent No.: US 6,174,301 B1
(45) Date of Patent: Jan. 16, 2001

(54) DUAL USE NEEDLE CAP

(76) Inventor: Roland B. Wilson, Jr., 64 Hillcrest Dr., Peru, IN (US) 46970

( * ) Notice: Under 35 U.S.C. 154(b), the term of this patent shall be extended for 0 days.

(21) Appl. No.: 09/230,714

(22) PCT Filed: Jun. 16, 1997

(86) PCT No.: PCT/US97/11071

§ 371 Date: Jan. 29, 1999

§ 102(e) Date: Jan. 29, 1999

(87) PCT Pub. No.: WO98/04306

PCT Pub. Date: Feb. 5, 1998

Related U.S. Application Data

(63) Continuation of application No. 08/681,852, filed on Jul. 29, 1996, now Pat. No. 5,667,496.

(51) Int. Cl.$^7$ ..................................... A61M 5/00
(52) U.S. Cl. ........................... 604/192; 604/263; 128/919
(58) Field of Search .................................. 604/192, 263, 604/187, 110; 128/919

(56) References Cited

U.S. PATENT DOCUMENTS

| | | |
|---|---|---|
| 4,659,330 | 4/1987 | Nelson et al. . |
| 4,950,242 | 8/1990 | Alvarez . |
| 4,982,842 | 1/1991 | Hollister . |
| 5,667,496 | * 9/1997 | Wilson, Jr. ........................... 604/263 |

* cited by examiner

Primary Examiner—John D. Yasko
(74) Attorney, Agent, or Firm—Baker & Daniels

(57) ABSTRACT

A dual use needle cap having a before use portion and an after use portion. The before use portion including an outer surface and an interior surface defining a chamber sized to enclose a needle of a syringe. The after use portion includes a clamp and a hood attached to the outer surface of the before use portion at opposite ends thereof. The clamp is configured to fit on to at least one of a barrel of a syringe or a needle assembly connected to the syringe and the hood is configured to cover a tip of the needle.

20 Claims, 5 Drawing Sheets

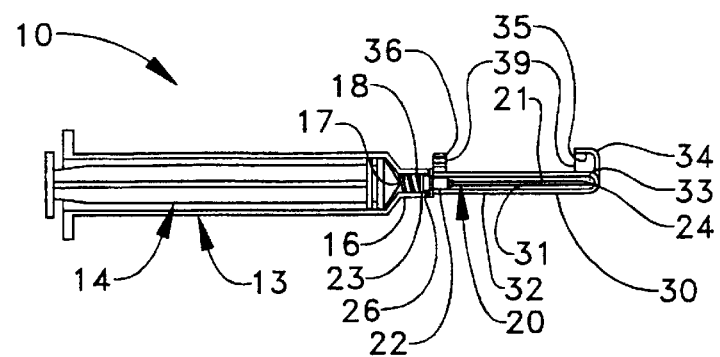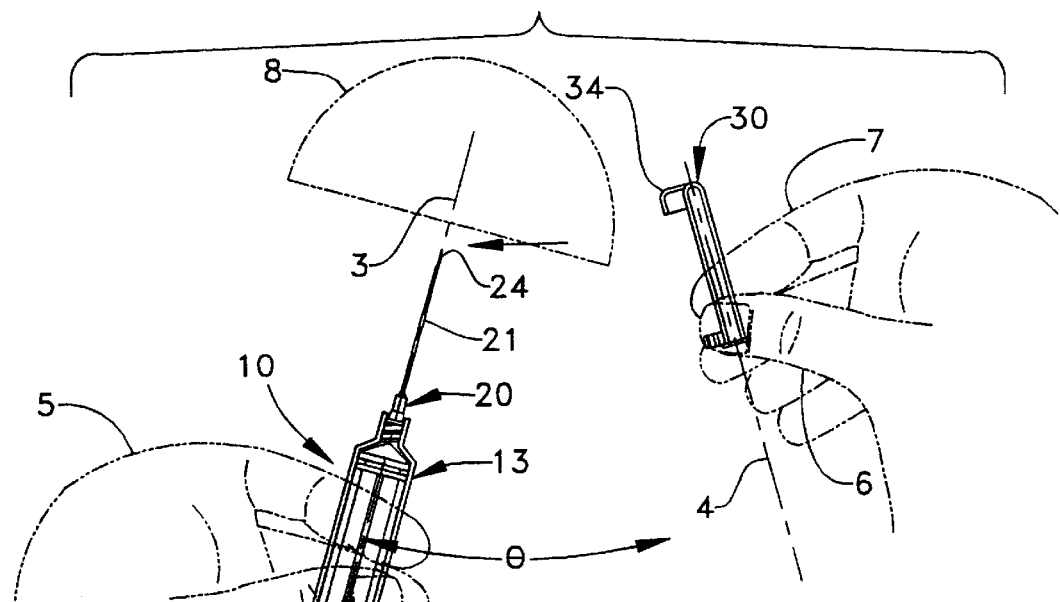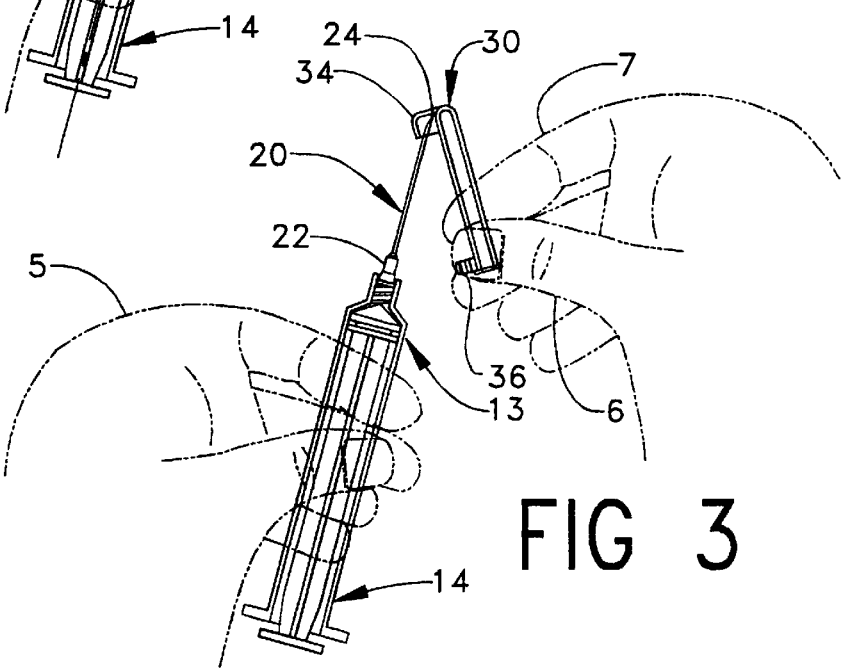

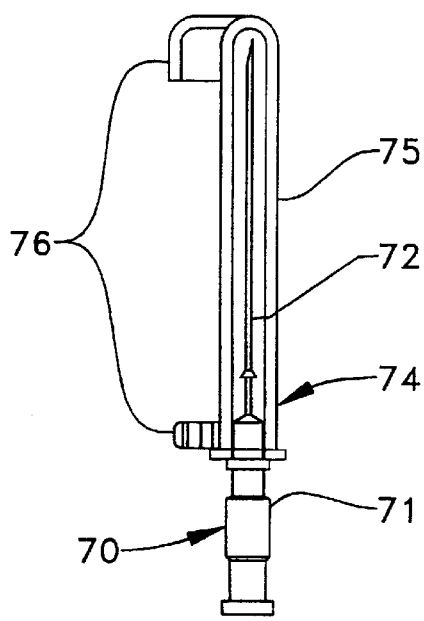
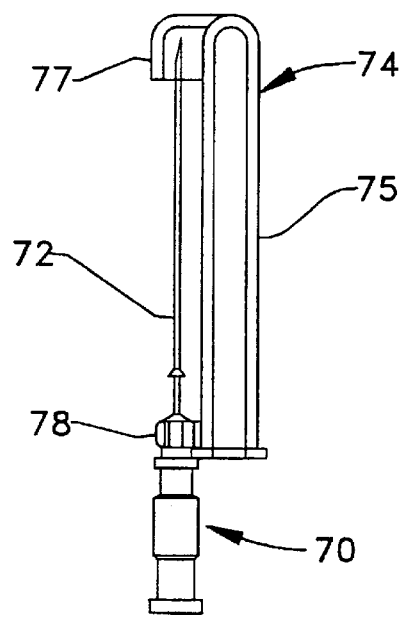
FIG 11
FIG 12
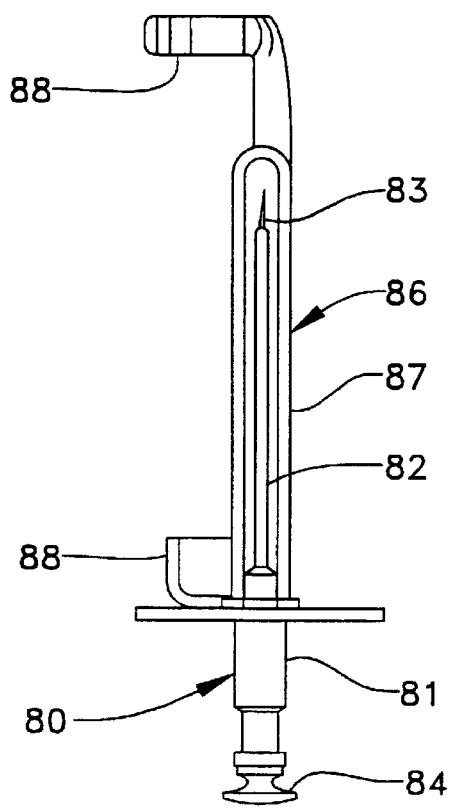
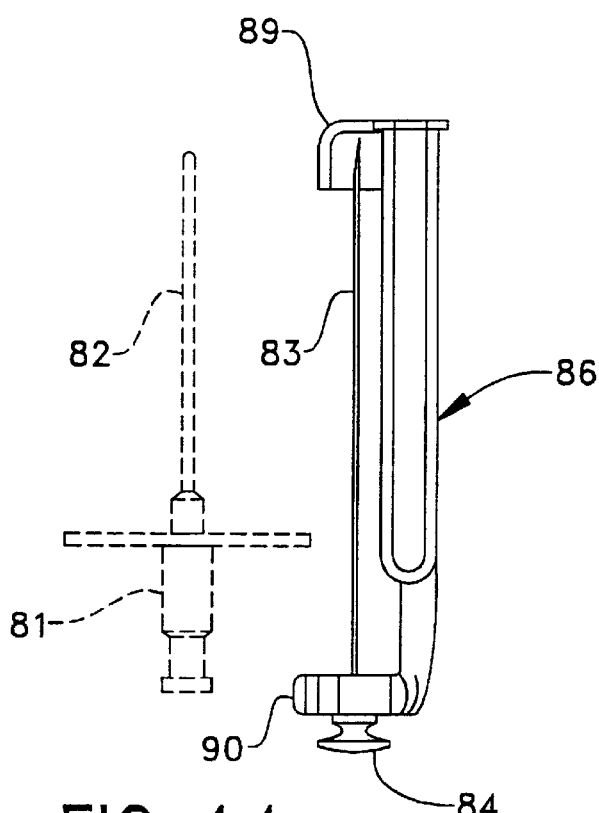
FIG 13
FIG 14

US 6,174,301 B1

DUAL USE NEEDLE CAP

This application is a continuation of U.S. Ser. No. 08/681,852 filed Jul. 29, 1996 now U.S. Pat. No. 5,667,496.

TECHNICAL FIELD

The present invention relates generally to caps for medical needles, and more particularly to an integrated dual use needle cap for before and after use of a syringe or other type of medical needle.

BACKGROUND OF THE INVENTION

The potential for an accidental needle stick is of great concern to health care providers because of the possible transmission of a deadly disease, such as a AIDS or Hepatitis. In some cases it is not always convenient for the health care provider to dispose of used needles in a sharps container during certain procedures, especially those involving the use of many syringes or needles. Thus, in these cases used syringes and/or needles often litter a treatment area while the patient is undergoing a procedure. Health care providers recognize a need to render these used needles harmless during a treatment, but without interrupting the procedure. While there is a myriad of different patented and unpatented devices for preventing accidental needle sticks, most are difficult or too expensive to manufacture, some are impractical and many more require separate pieces instead of being incorporated into the needle assembly or syringe. The present invention is directed to overcoming these and other problems associated with prior art devices and methods for preventing accidental needle sticks.

SUMMARY OF THE INVENTION

A syringe with a dual use needle cap comprises a barrel and a plunger mounted to move within the barrel. A needle assembly has a base end attached to the barrel, and a needle attached to and protruding away from the base. A dual use cap has a before use portion integrated with an after use portion. The before use portion has an outer surface and an interior surface defining a sterile chamber sized to enclose the needle. The after use portion includes a living clamp and a hood attached to the outer surface adjacent opposite ends of the dual use cap. The living clamp is sized to snap fit onto at least one of the barrel or the needle assembly. Finally, the hood is sized to cover the tip of the needle.

In another embodiment of the present invention, a dual use needle cap consists essentially of a single piece of plastic that is molded to include a before use portion integrated with, but separate from, an after use portion. The before use portion has an outer surface and an interior surface defining a sterile chamber sized to enclose and maintain sterility of a needle before use. The after use portion includes a living clamp and hood molded on the outer surface adjacent its opposite ends. The living clamp is sized to snap fit onto at least one of a needle assembly or a barrel of a syringe. The hood is sized to cover the tip of a needle after use.

One object of the present invention is to reduce the risk of accidental needle sticks.

Another object of the present invention is to provide a practical yet safe method of covering used syringes and other medical needles in some medical situations.

Still another object of the present invention is to provide a simple and inexpensive way of introducing additional safety into every syringe or other medical needle assembly.

Another object of the present invention is to provide a visual indication of whether a syringe or other medical needle is sterile or used.

Still another object of the present invention is to provide an improved cap for needle assemblies.

BRIEF DESCRIPTION OF THE DRAWINGS

FIG. 1 is a side elevational view of a syringe according to the present invention, before being used.

FIG. 2 is a side elevational view of a syringe recapping procedure according to the present invention.

FIG. 3 is a side elevational view of a pivot portion of a syringe recapping procedure according to the present invention.

FIG. 11 is a side elevational view of a regional block needle assembly according to still another embodiment of the present invention, before being used.

FIG. 12 is a side elevational view of the needle assembly of FIG. 11, after being used.

FIG. 13 is a side elevational view of a radiology needle assembly with cannula according to another embodiment of the present invention, before being used.

FIG. 14 is a side elevational view of the radiology needle and cannula of FIG. 13, after being used.

DETAILED DESCRIPTION OF PREFERRED EMBODIMENT

Figure 4:
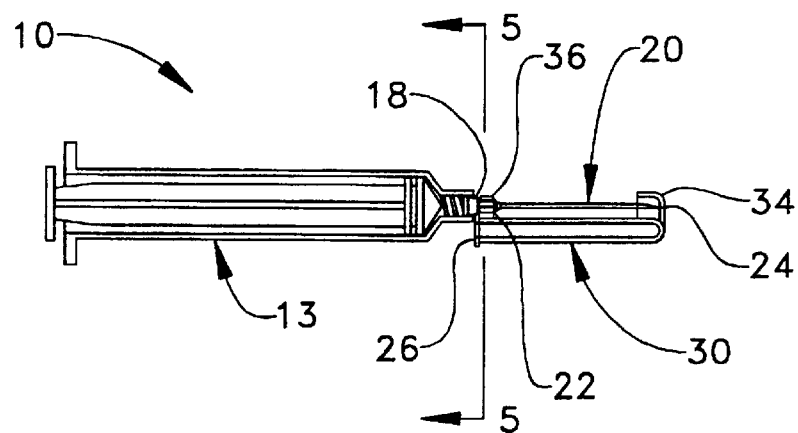
FIG. 4 is a side elevational view of a syringe according to the present invention, after being used.

Referring now to FIG. 1, a syringe with a dual use needle cap 10 is illustrated in its sterile condition before being used. Syringe 10 is substantially identical to syringes commercially available except for the inclusion of an after use portion 39 molded on the outer surface 32 of cap 30. In all other ways, syringe 10 is similar to commercially available syringes in that it includes a barrel 13 with a relatively large diameter portion within which moves a plunger 14 and a smaller diameter neck 16 protruding from the end of the large diameter portion. A needle assembly 20 is typically threadably or snap-fit attached to barrel 13, and is covered by dual use needle cap 30.

Needle assembly 20 includes a base 22 and a needle 21 attached to and protruding away from the base. Base 22 is attached to barrel 13 by a typical snap-fit (not shown) or a Luer thread 23 received in inner threads 17 of neck 16. Needle 21 includes a tip 24. Before being used, needle 21 is kept sterile by the dual use needle cap 30 in a manner well known in the art. Dual use needle cap 30 includes an outer surface 32 and an inner surface 31 that defines a sterile chamber 33, which is sized to enclose and maintain the sterility of needle 21. Dual use needle cap 30 snap fits onto base 22 of needle assembly 20 such that a small clearance preferably exists between end 26 of cap 30 and end 18 of barrel 13.

Cap 30 is preferably made from a typical medical grade plastic to include an after use portion 39 molded onto outer surface 32. After use portion 39 includes a hood 34 and a living clamp 36 molded adjacent opposite ends of dual use needle cap 30. In this embodiment, hood 34 opens in the same direction as sterile chamber 33 and is sized to cover tip 24 rather than the complete needle 21. In other words, hood 34 has a depth 35 substantially shorter than the length of needle 21. Interior surface 31 preferably includes molded surfaces that prevent cap 30 from being advanced too far on needle assembly 20 that tip 24 penetrates through outer surface 32.

The syringe is uncapped in a typical fashion by simply pulling cap 30 away from barrel 13 using two hands. In some medical situations, several needles are used in relatively quick succession in an area not convenient for quick disposal in a sharps container. In such situations, it would be desirable to render each needle relatively harmless with a safe procedure, before the syringe is laid down in the treatment area. The present invention is ideally suited for this type of medical situation. If the present invention were made a standard part of all syringes, then the after use portion would always be available as a relatively safe way of recapping a needle when a sharps container is not readily convenient.

Referring now to FIGS. 2 and 3, a recapping procedure according to the present invention is illustrated. The goal of this procedure is to maintain the provider's fingers 6 and 7 outside of a needle stick danger zone 8 that is located adjacent tip 24 of needle 21. The syringe 10 is held in one hand 5, and the dual use needle cap 30 is preferably held between the thumb 6 and index finger 7 of the person's other hand. Syringe 10 can be thought to have an axis 3 that is at a substantial angle theta with respect to an imaginary axis 4 running through dual use needle cap 30. While maintaining this angle, which is generally on the order of about 5 to 45 degrees, cap 30 is advanced toward needle 21 while generally maintaining the angle until tip 24 engages hood 34. After tip 24 engages hood 34 as shown in FIG. 3, dual use needle cap 30 is pivoted about tip 24 until living clamp 36 snaps onto base 22 of needle assembly 20.

FIG. 4 shows syringe 10 after being used in a conventional manner and then recapped and rendered relatively safe according to the present invention. In this condition, dual use needle cap 30 is attached to syringe 10 by hood 34 covering tip 24 and living clamp 36 gripping base 22 of needle assembly 20. Hood 34 may be filled with a material, such as foam or glue, to further grip needle tip 24. In this embodiment, dual use needle cap 30 is sized to be about the same length as needle assembly 20, such that end 26 comes into contact with end 18 of barrel 13 before tip 24 protrudes through the outer surface of hood 34. In this condition, the syringe clearly and visually reveals itself as having already been used. Also, by recapping the needle, any danger of an accidental needle stick with a used syringe is substantially reduced. After a medical procedure, the used syringes can be gathered relatively safely and then disposed of in a sharps container. During the procedure, the individual used syringes pose a relatively low threat to the health care providers working in the treatment area.

Figure 5:
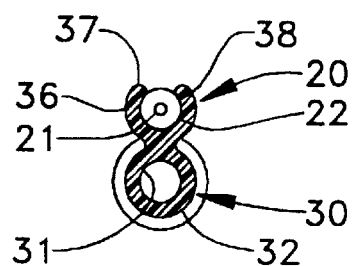
FIG. 5 is a sectioned top elevational view taken along section lines 5—5 of FIG. 4.

FIG. 5 shows a sectioned view of living clamp 36, which is molded on the outer surface 32 of dual use needle cap 30. Living clamp 36 includes a first curved arm 37 and a second curved arm 38 that are sized, in this embodiment, to snap fit onto the cylindrically shaped base 22 of needle assembly 20. Those skilled in the art will appreciate that needle assemblies 20 can come with a wide variety of generally cylindrically shaped bases. As used in this patent, the term cylindrical refers to regular cylinders, frusto-conical shapes, and bases having one or more irregular, or non-circular, cross sections. For instance, those skilled in the art would realize that a suitable living clamp could be shaped for attachment to a base having a square cross section.

Figure 6:
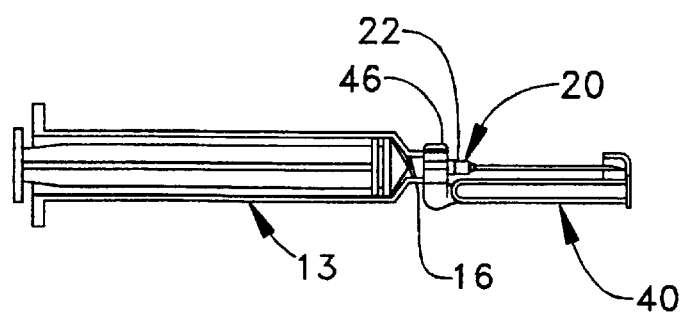
FIG. 6 is a side elevational view of a syringe according to another embodiment of the present invention, after being used.
Figure 7:
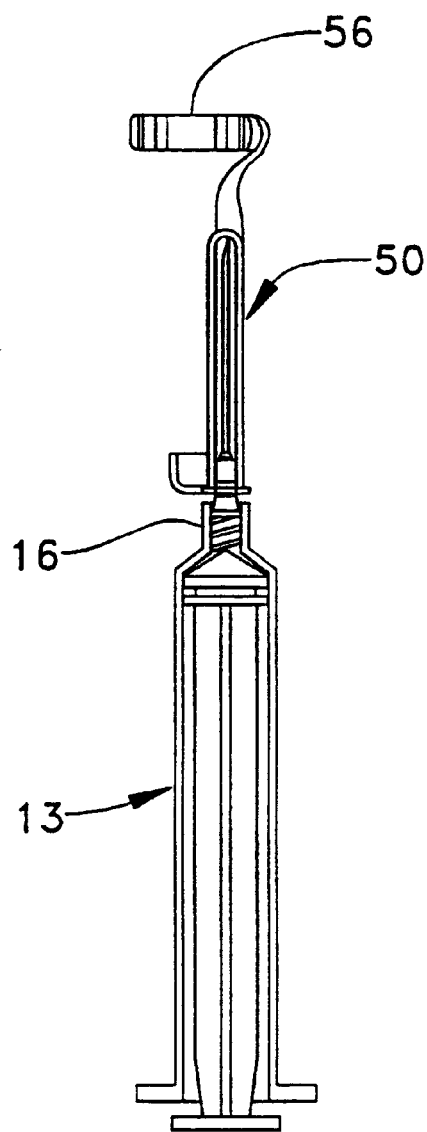
FIG. 7 is a side elevational view of a syringe according to still another embodiment of the present invention, before being used.
Figure 8:
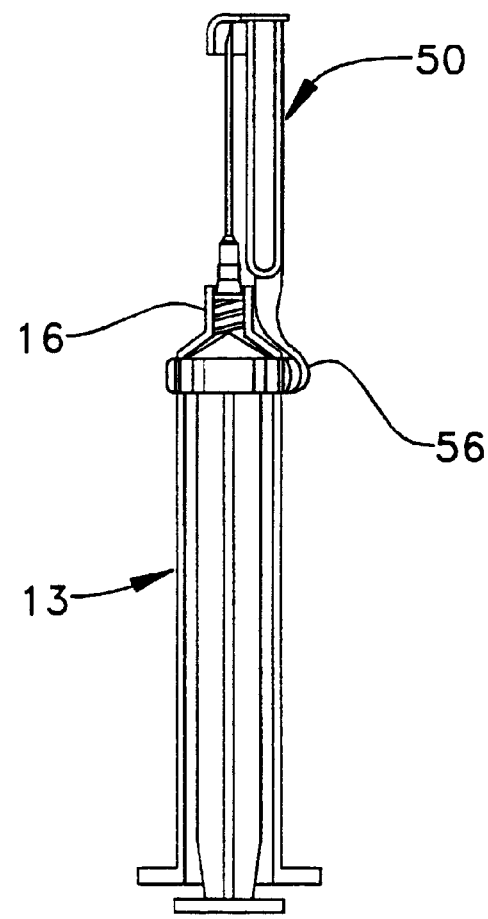
FIG. 8 is a side elevational view of the syringe of FIG. 7, after being used.

Those skilled in the art will appreciate that the above description is intended for illustrative purposes only and is not intended to limit, in any way, the actual and intended scope of the present invention. For instance, the present invention could be modified by sizing and locating the living clamp to snap fit onto the neck 16 of the barrel 13 instead of the base 22 of the needle assembly 20 (see FIG. 6). Also, the dual use needle cap of the present invention could be modified from that shown by positioning the hood 34 and living clamp 36 at opposite ends as shown in FIGS. 6–8. In this way, the hood would open in an opposite direction to that of the sterile chamber and would provide a further visual clue as to the fact that a particular syringe has been used.

Figure 9:
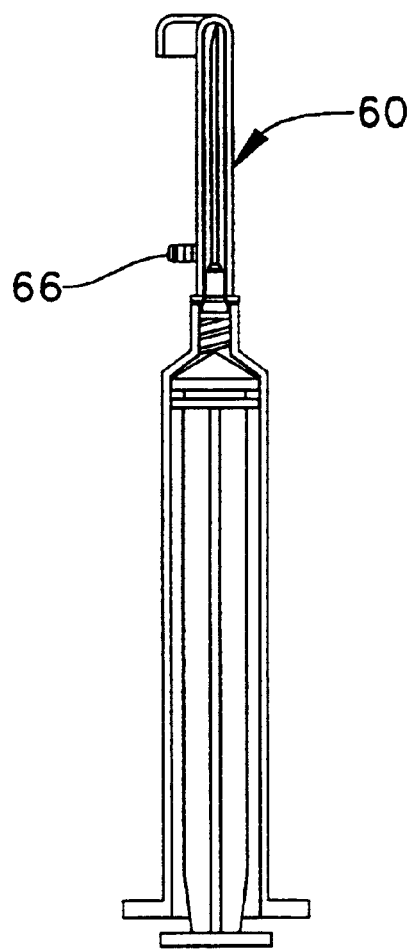
FIG. 9 is a side elevational view of a syringe according to another embodiment of the present invention, before being used.
Figure 10:
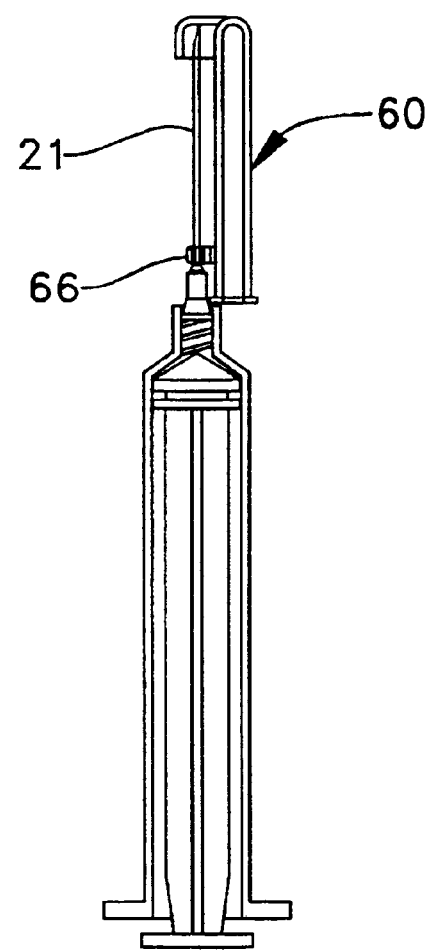
FIG. 10 is a side elevational view of the syringe of FIG. 9, after being used.

Referring now to FIG. 7 and 8, still another embodiment of the present invention is illustrated. In this embodiment, dual use needle cap 50 includes a living clamp portion 56 that is sized to snap-fit onto the relatively large diameter portion of barrel 13, rather then the neck portion 16 as in the embodiment shown in FIG. 6. FIG. 7 shows the syringe before being used with the needle enclosed in a sterile chamber. FIG. 8 shows the syringe after being used with the needle rendered relatively safe after being recapped with dual use needle cap 50 according to the present invention. Referring now to FIGS. 9 and 10, still another embodiment of the present invention is illustrated. This embodiment is substantially similar to the previous embodiments except that dual use needle cap 60 snap-fits to the needle 21 itself rather than to the base of the needle assembly, the neck of the barrel or the large diameter portion of the barrel as in the previous embodiments.

Referring now to FIGS. 11–14, those skilled in the art will appreciate that the present invention finds potential application in medical needle assemblies other than syringes. For instance, FIGS. 11 and 12 show a regional block needle assembly 70 with a dual use needle cap 74 according to the present invention, before and after use respectively. Regional block needle assembly 70 includes a base 71 with a needle 72 attached to and protruding away from base 71. Like the previous embodiments, dual use needle cap 74 includes a before use portion 75 that is sized to cover and maintain the sterility of needle 72. Dual use needle cap 74 also includes an after use portion 76 molded on the outer surface of the before use portion to include a hood 77 and a living clamp 78 sized to snap-fit onto base 71. FIGS. 13 and 14 show still another example of the present invention in relation to a radiology needle with cannula assembly 80 covered by a dual use needle cap 86 according to the present invention. In this case, the radiology needle assembly includes a base 81 having a cannula 82 attached to and protruding away from base 81. The two part device also includes a needle 83 that is received into cannula 82 and attached at its base end to a handle 84. Like the previous embodiments, dual use needle cap 86 includes a before use portion 87 that is sized to cover and maintain the sterility of needle 83 and cannula 82, and an after use portion 88 that is sized to render needle 83 safe after being used. After the needle 83 and handle 84 are withdrawn from cannula 82 and base 81, which is usually left in the patient, dual use needle cap 86 is used to render needle 83 relatively safe in the same procedure described in relation to the earlier embodiments so that hood 89 covers the tip of needle 83 and living clamp 90 snaps onto the bottom of needle 83 above handle 84.

Although not specifically shown, the present invention could find potential application in a wide variety of surgical and anesthetic procedural trays. These include but are not limited to regional block anesthesia trays, spinal trays, epidural trays, incision and drainage kits, thorasentesis trays, and a variety of other kits or trays including those used for amniosentesis, peritineosentesis, peritineal lavage and suprapubic catheter placement. The present invention could also be used in relation to aspiration kits, soft tissue and bone biopsy kits or trays or any percutaneous needle placement kits or subcutaneous intramuscular needles, as well as possibly used in conjunction with intravascular placement of catheters. In many of these suggested applications, the physician is provided with a tray or kit that includes several different sized or shaped needle assemblies that can often litter a treatment area in an unsafe uncovered condition before the particular treatment is completed. It is not always convenient to position a sharps container near the treatment area or temporarily halt a particular treatment just to dispose of a single needle in a sharps container located at some distance from the treatment area. Most of these applications could benefit by including with the needle assemblies a dual use needle cap according to the present invention so that the various needles could be rendered relatively harmless before they are laid down in the treatment area. After the treatment, the various covered needle assemblies can be gathered and disposed of in an appropriate sharps container. All of the above examples and suggested applications are for illustrative purposes only and are not intended to limit the scope of the present invention in any way. Those skilled in the art will no doubt find other applications not specifically identified, but which are still intended to be covered under the intended scope of the present invention, which is defined in terms of the claims set forth below.

I claim:

1. A syringe with a dual use needle cap comprising:
   a barrel;
   a plunger with a portion mounted to move within said barrel;
   a needle assembly attached to said barrel; and
   a dual use cap with a before use portion integrated with an after use portion, and said before use portion having an outer surface and an interior surface defining a sterile chamber sized to enclose said needle, and said after use portion including a living clamp and a hood attached to said outer surface adjacent opposite ends of said dual use cap, and said living clamp being sized to snap fit onto at least one of said barrel and said needle assembly, and said hood being sized to cover a tip of said needle.

2. The syringe of claim 1 wherein said needle has a length; and
   said hood has a depth substantially shorter than said length.

3. The syringe of claim 1 wherein said dual use cap has a length that is about the same as a length of said needle assembly.

4. The syringe of claim 1 wherein said needle defines a first axis;
   said after use portion of said dual use cap defines a second axis; and
   said tip of said needle can enter said hood when said second axis is at a substantial angle relative to said first axis.

5. The syringe of claim 1 wherein said living clamp is sized to clamp onto said base of said needle assembly.

6. The syringe of claim 1 wherein said hood opens in a same direction as said sterile chamber.

7. The syringe of claim 1 wherein said hood opens in a direction opposite to that of said sterile chamber.

8. A needle assembly with a dual use cap comprising:
   a base;
   a needle with a tip on one end and an opposite end attached to said base; and
   a dual use cap molded from a single piece of plastic to have a before use portion integrated with, but separate from, an after use portion;
   said before use portion having an outer surface and an interior surface defining a sterile chamber sized to enclose said needle;
   said after use portion including a living clamp and a hood attached to said outer surface adjacent opposite ends of said dual use cap, and said living clamp being sized to snap fit onto said base, and said hood being sized to cover said tip.

9. The needle assembly of claim 8 wherein said needle has a length; and
   said hood has a depth substantially shorter than said length.

10. The needle assembly of claim 9 wherein said dual use cap has a first length;
    said needle combined with said base has a second length that is about the same as said first length.

11. The needle assembly of claim 8 wherein said needle defines a first axis;
    said after use portion of said dual use cap defines a second axis; and
    said tip of said needle can enter said hood when said second axis is at a substantial angle relative to said first axis.

12. The needle assembly of claim 8 wherein said hood opens in substantially a same direction as said sterile chamber.

13. The needle assembly of claim 8 wherein said hood opens in a direction opposite to that of said sterile chamber.

14. A dual use needle cap consisting essentially of:
    a single piece of plastic having opposite ends and being molded to include a before use portion integrated with, but separate from, an after use portion;
    said before use portion having an outer surface and an interior surface defining a sterile chamber sized to enclose and maintain sterility of a needle before use;
    said after use portion including a living clamp and a hood molded on said outer surface adjacent said opposite ends, and said living clamp being sized to snap fit onto at least one of a needle assembly and a barrel of a syringe, and said hood being sized to cover a tip of said needle after use.

15. The dual use needle cap of claim 14 wherein said needle has a length; and
    said hood has a depth substantially shorter than said length.

16. The dual use needle cap of claim 14 having a length that is about the same as a length of said needle assembly.

17. The dual use needle cap of claim 14 wherein said needle defines a first axis;
    said after use portion of said dual use cap defines a second axis; and said tip of said needle can enter said hood when said second axis is at a substantial angle relative to said first axis.

18. The dual use needle cap of claim 14 wherein said living clamp is sized to clamp onto a base of said needle assembly.

19. The dual use needle cap of claim 14 wherein said hood opens in a same direction as said sterile chamber.

20. The dual use needle cap of claim 14 wherein said hood opens in a direction opposite to that of said sterile chamber.

* * * * *